US 6,656,197 B1

(12) United States Patent
LaHaye

(10) Patent No.: US 6,656,197 B1
(45) Date of Patent: Dec. 2, 2003

(54) MULTI-FUNCTION SURGICAL INSTRUMENT FOR FACILITATING OPHTHALMIC LASER SURGERY

(76) Inventor: Leon C. LaHaye, 566 Sand Pit Rd., Arnaudville, LA (US) 70512

( * ) Notice: Subject to any disclaimer, the term of this patent is extended or adjusted under 35 U.S.C. 154(b) by 0 days.

(21) Appl. No.: 10/071,430

(22) Filed: Feb. 8, 2002

Related U.S. Application Data

(63) Continuation-in-part of application No. 09/960,582, filed on Sep. 21, 2001, now Pat. No. 6,569,153, which is a continuation-in-part of application No. 08/894,264, filed on Jun. 28, 2001, now Pat. No. 6,497,700.

(51) Int. Cl.$^7$ ................................................. A61F 9/00
(52) U.S. Cl. ........................ 606/166; 606/4; 606/5; 604/289; 604/294; 604/301
(58) Field of Search .......................... 606/4–6, 166; 607/88–92; 604/294–298, 300–325, 289, 290

(56) References Cited

U.S. PATENT DOCUMENTS

| 4,905,711 A | * | 3/1990 | Bennett et al. ............. 128/869 |
| 5,009,660 A | * | 4/1991 | Clapham .................... 606/166 |
| 5,108,412 A | * | 4/1992 | Krumeich et al. .......... 606/166 |
| 5,336,215 A | * | 8/1994 | Hsueh et al. ................... 606/4 |
| 5,616,139 A | * | 4/1997 | Okamoto ......................... 606/4 |
| 5,624,456 A | * | 4/1997 | Hellenkamp ................ 606/166 |
| 5,807,380 A | * | 9/1998 | Dishler ............................ 606/5 |
| 5,980,543 A | * | 11/1999 | Carriazo et al. ............ 606/166 |
| 6,090,199 A | * | 7/2000 | Wallace, Jr. et al. ........ 606/166 |
| 6,099,541 A | * | 8/2000 | Kloptek ....................... 606/166 |
| 6,126,668 A | * | 10/2000 | Bair et al. ................... 606/166 |
| 6,228,099 B1 | * | 5/2001 | Dybbs ......................... 606/166 |
| 6,344,040 B1 | * | 2/2002 | Juhasz et al. ................... 606/4 |
| 6,349,726 B1 | * | 2/2002 | Graczyk ...................... 128/858 |
| 6,350,272 B1 | * | 2/2002 | Kawesch ..................... 606/166 |
| 6,497,700 B1 | * | 12/2002 | LaHaye .......................... 606/4 |

* cited by examiner

Primary Examiner—Roy D. Gibson
(74) Attorney, Agent, or Firm—Joseph L. Lemoine, Jr.

(57) ABSTRACT

The multi-function surgical instrument for facilitating corneal surgery by laser includes lower and upper rings. Lower ring includes a wall structure about a central aperture. Wall of the lower ring isolates a cornea disposed within the central aperture. Drainage system of the lower ring is used to control hydration of corneal tissue disposed in the central aperture. Platform of the lower ring isolates and prevents excessive hydration of a corneal flap reposed thereon. Upper ring includes a plurality of passages having directed ports and may be used to evacuate plume, direct beneficial fluids or gases onto tissues below.

24 Claims, 6 Drawing Sheets

(Section A-A)

US 6,656,197 B1

MULTI-FUNCTION SURGICAL INSTRUMENT FOR FACILITATING OPHTHALMIC LASER SURGERY

This patent application is a continuation-in-part application of presently pending U.S. patent application Ser. No. 09/960,582 filed Sep. 21, 2001, now U.S. Pat. No. 6,569,153 B1, which is a continuation-in-part application of presently pending U.S. patent application Ser. No. 08/894,264 filed Jun. 28, 2001 now U.S. Pat. No. 6,497,700 B1.

FIELD OF THE INVENTION

In the field of ophthalmic surgery the use of lasers is well known. In laser assisted in-situ kerotomileusis pulses of laser light are used to ablate desired portions of the stromal bed following temporary removal of the outer tissues of the cornea. After replacement of the temporarily removed tissues the cornea is reshaped. During such procedure, and other ophthalmic procedures involving ablation of eye tissue, positioning and fixation of the eye against movement is important, as is proper tissue hydration, control of smoke, plume and splatter, maintaining cleanliness of open tissues, etc. The invention disclosed and claimed herein relates to a multifunction instrument placed on the surface of the eye during ablative eye surgery to assist the ophthalmic surgeon to perform laser ablative eye surgery.

BACKGROUND OF THE INVENTION

In corneal surgery the use of lasers is well known. In such procedures precisely controlled pulses of laser light are used to remove thin layers of tissue by ablation. For instance, in photorefractive keratectomy ("PRK") the cornea is reshaped by first removing the epithelium and Bowman's layer (by various means) and ablating the stromal bed by laser (after which the epithelium and Bowman's layer are left to re-form by healing). In laser assisted in-situ kerotomileusis ("LASIK") the cornea is reshaped by temporarily removing the outer layers (epithelium, Bowman's layer and a portion of the stromal bed) thereof by sharp instrument, ablating selected areas of the underlying stromal bed by laser and then replacement of the removed tissues. Various other corneal surgery is also performed using a laser to ablatively remove selected eye tissue.

There procedures encounter some common challenges. Removed tissues must be set aside. The removed tissues should be set aside to a location which is clean, sterile, and where over or under hydration can be prevented. This is particularly problematic in LASIK where the outer layers of tissue (commonly called the corneal "flap") typically remains attached to the eye by a "hinge" of tissue. The exposed stromal bed of the eye should also be protected from migration of exterior eye fluids, which may contain debris and/or bacteria and from either excessive or over hydration.

The eye must be positioned properly, and fixed against movement therefrom, so that laser pulses are applied, consistently, to only the selected tissues. Both the patient and the physician should be protected from airborne smoke, plume and splatter. Following ablation, the opened tissues should be well cleansed while maintaining proper hydration, and the temporarily removed tissues replaced with minimal handling.

The invention disclosed and claimed herein is a multi-function surgical instrument directed to each of the above-mentioned issue. It provides a convenient location to store temporarily removed tissues. It provides a means to isolate both stromal bed and removed tissues from cul-de-sac fluids. It provides means to fix the position of the eye as desired. It provides means for controlling hydration of open tissues. It provides means for removal of smoke, plume and splatter. It provides means for facily cleansing open tissues prior to closure. It provides means to facilitate replacement of removed tissues with minimal handling.

Other art discloses ophthalmic tools which includes some, but not all, of the features of the multifunction tool herein disclosed and claimed. For instance U.S. Pat. No. 5,108,412 to Rosenbaum et al disclose a suction ring for attachment to the sclera in the limbal plane. This apparatus is used to guide a trepan perpendicularly to the limbal plane. In U.S. Pat. No. 5,980,543 to Carriazo et al a similar suction ring is used to guide a microkeratome parallel to the limbal plane. In neither of these patents is the suction ring used to fix the position of the eye during ablation. In neither of these patents does the suction ring include a platform for "storage" and replacement of a corneal flap during a surgical procedure. In neither of these patents are other attributes of the invention, such as plume and splatter evacuation means, means for creating flow of dehydrating gas over the aperture of the ring, means for improved irrigation for a surgical field, etc., disclosed.

Likewise U.S. Pat. Nos. 5,941,873 and 5,971,977 to Korenfeld shows one, but not other, attributes of the invention disclosed and claimed herein. In these patents there is disclosed a device having a ring-shaped tube with a plurality of apertures disposed about the inner circumference thereof, to aid in smoke, plume and splatter removal during an ablative procedure of the eye. These patents do not teach any structure for aspirating liquid away from an open stromal bed nor do they teach a sterile platform for storage and replacement of removed tissues.

The invention herein disclosed and claimed is directed to provision of a surgical instrument to facilitate the opthalmic surgeon accomplishing a plurality of desirable objectives associated with laser surgery of the eye, particularly LASIK, including isolation, controlling hydration and cleansing of open tissues; storage and replacement of temporarily removed tissues; positioning and fixation of the eye; and removal of smoke, plume and splatter.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

Figure 1:
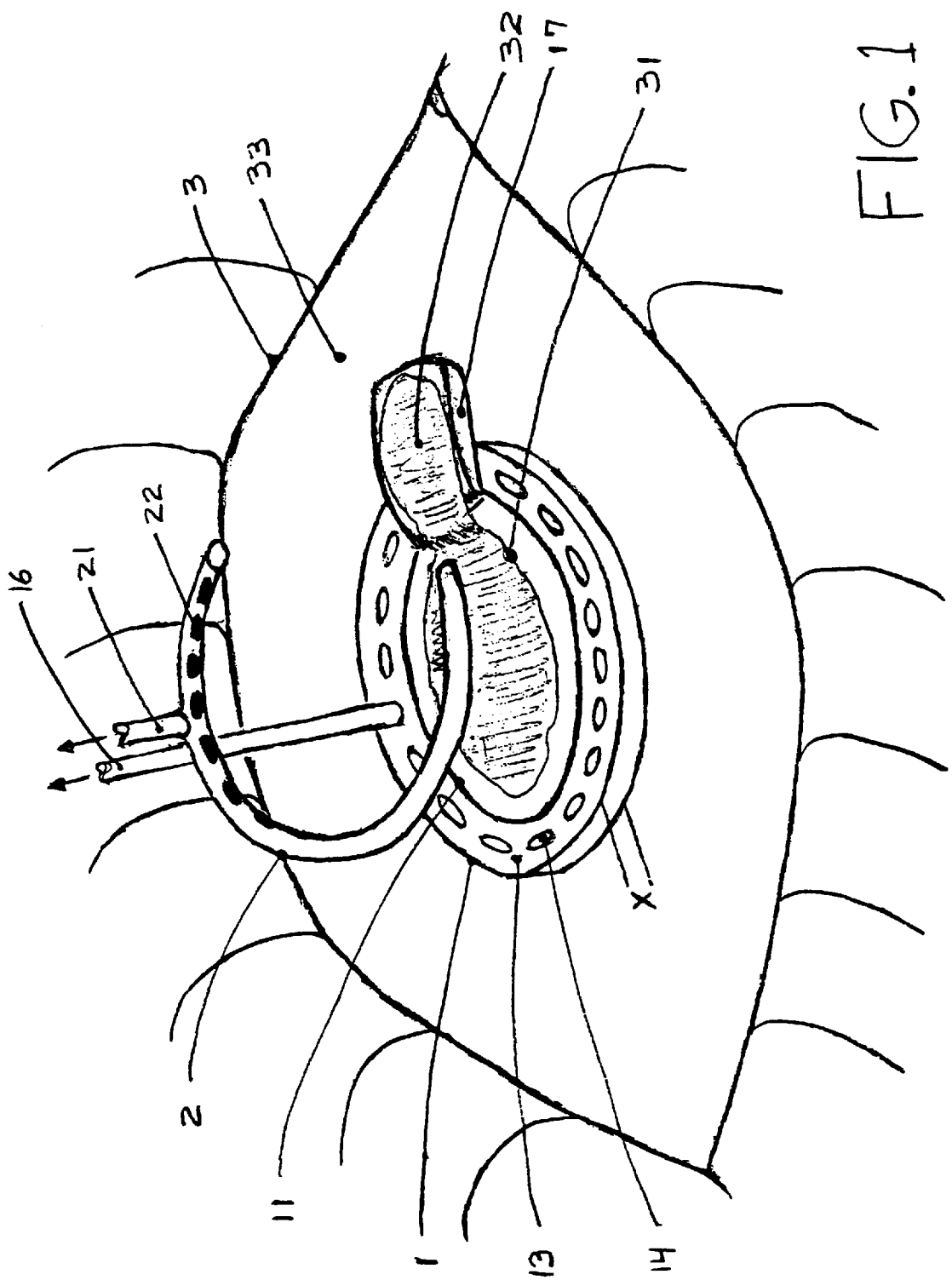
FIG. 1 is a perspective view of the preferred embodiment of the disclosed and claimed invention in the preferred, nasal, position on a patient's eye with an open stromal bed.
Figure 1A:
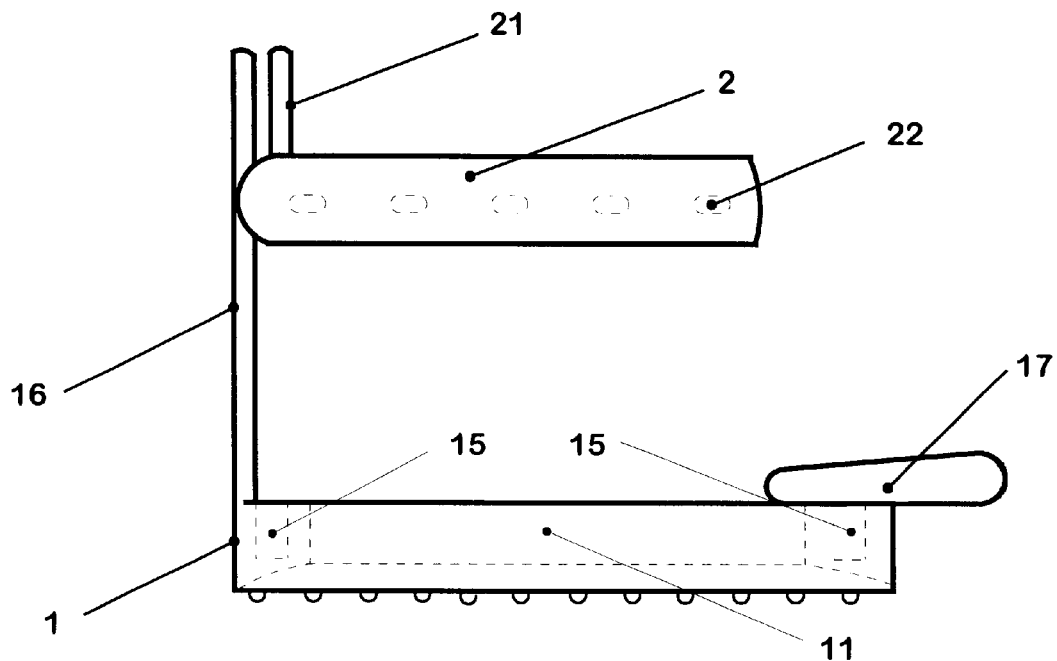
FIG. 1a is an elevational view of an embodiment of the invention shown in FIG. 1.

FIG. 1 is a schematic view of one embodiment of the surgical instrument of the present invention in position on a human eye 3. FIG 1a depicts the instrument of FIG. 1 in elevational view. Shown are two generally superposed ring-shaped structures, lower ring 1 and upper ring 2, the structure and purpose of which will be herein described in enabling detail.

Figure 2A:
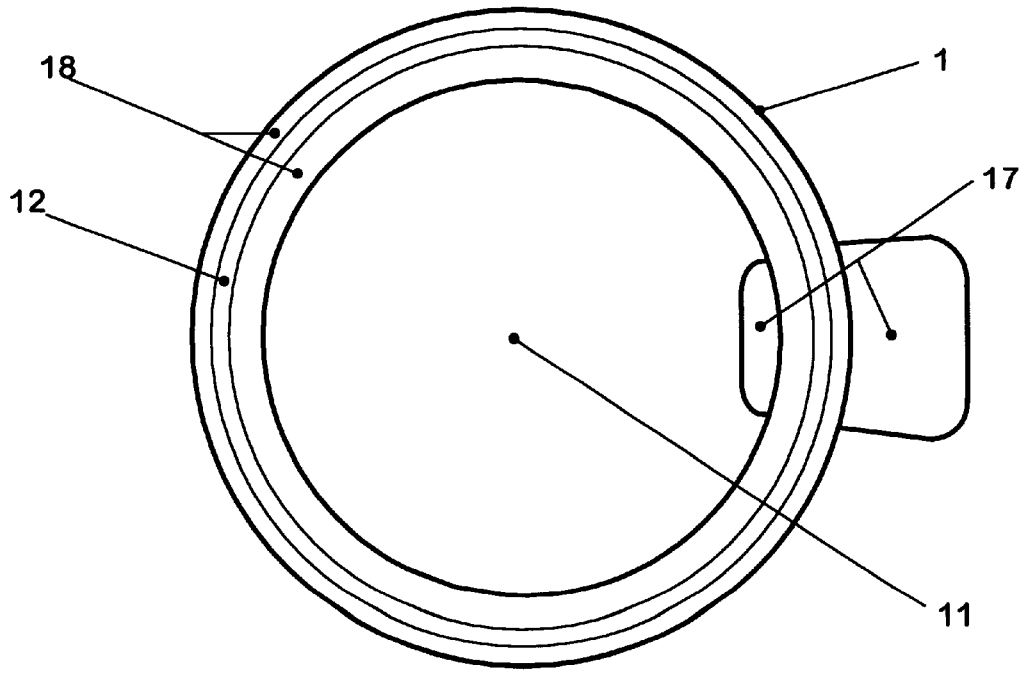
FIG. 2a is a bottom plan view of the lower surface of the lower ring of the present invention.
Figure 2:
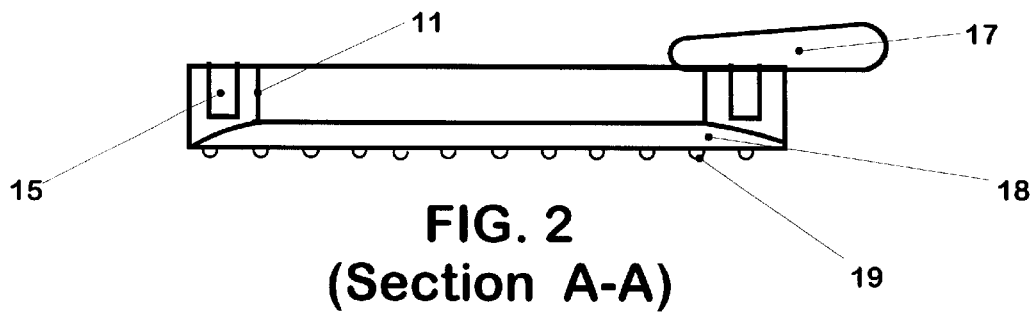
FIG. 2 is a perspective view of the lower surface of the lower ring of an alternative embodiment of the present invention.

Lower ring 1 has several functions. Its central aperture 11 is sized approximately that of the circumference of the limbus, thus "capturing" the corneal bulge of the eye. In the preferred embodiment of the invention the lower surface 18 of said ring will be a concave surface matching the curvature of the sclera 33. Therefore, both "capture" of the limbus by the aperture 11, and frictional engagement of lower surface 18 with sclera 33 tends to fix position of the eye with respect to lower ring 1. Even more firm fixation of lower ring 1 to the eye (thus ability to control position of the eye by controlling the position of lower ring 1) may be accomplished by one or more other means, such as application of a vacuum between sclera 33 and lower surface 18, set of protuberances ("teeth") 19 on said lower surface of said ring (such as illustrated in FIG. 2) and/or one or more annular ridges 12 spaced radially apart on lower surface 18 as illustrated in FIG. 2a. In addition to providing firmer fixation of lower ring 1 to the eye, annular ridges 12 form an enhanced barrier to the passage of eye fluids from the sclera 33, which may contain undesirable debris, chemicals and bacteria into the area of the eye contained within aperture 11, and in particular into the open stromal bed 31, when lower ring 1 is in position on the eye.

Figure 3A:
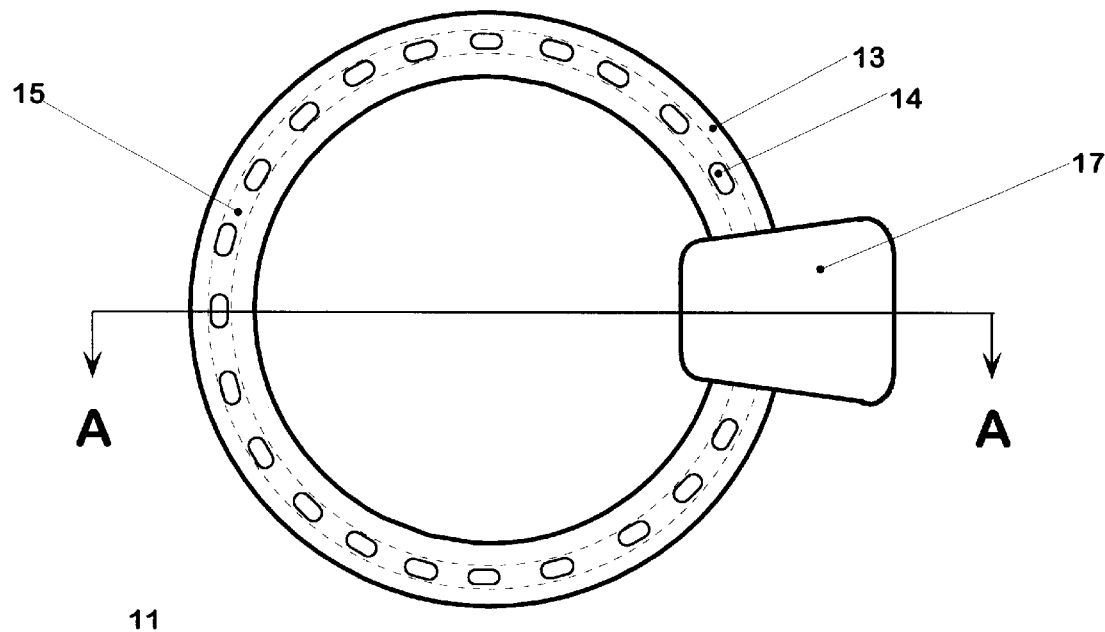
FIG. 3a is an elevational view of the lower ring of the preferred embodiment of the present invention.
Figure 3B:
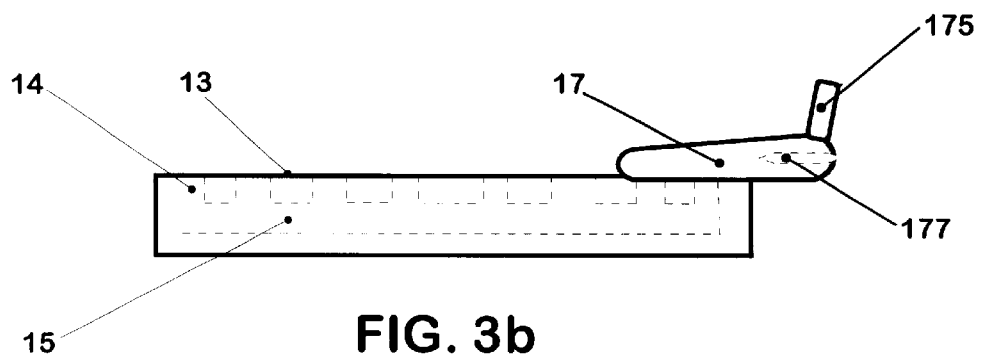
FIG. 3b is a top plan view of the lower ring of the preferred embodiment of the present invention.

Lower ring 1 also provides means to control hydration of the eye tissues which have been opened and/or are being ablated by laser. For example, referring to FIG. 1, in LASIK an open stromal bed 31 is created by removal of corneal flap 32 (by folding said flap onto platform 17). The height of lower ring 1, represented by dimension X, is such that the upper surface 13 of said ring is at, or preferably slightly below, the surface of stromal bed 31; so that excess liquids from said tissues will tend to flow radially outward and onto upper surface 13 of said ring. Yet at the same time, height X provides a physical barrier to outside fluids, such as will be on sclera 33, from flowing onto the area of the eye contained within aperture 11. The upper surface of said ring may also be inclined downward from aperture 11 to aid flow of liquid in a radially outward direction. Thus fluids emanating from stromal bed 31 tend to flow outward and away from said bed. This radial outward flow of fluids is aided by flow of air and fluids into ports 14 disposed in the upper surface 13 of lower ring 1. As is shown in FIGS. 3a and 3b ports 14 are interconnected by annular passage-way 15 disposed within lower ring 1. Said passage-way is connected to vacuum means by tube 16. In addition to aspirating excess liquids from stromal bed 31, the flow of air into ports 14 tends to create a flow of air over said stromal bed. Thus, the flow of air not only tends to move excess outwardly, it also tends to evaporate excess fluids on stromal bed 31. Thus by controlling the intensity of the vacuum applied to tube 16 the surgeon can control hydration of stromal bed 31. The size of ports 14 may increase in proportion to increased distance from tube 16 so as to cause the flow of air to be more uniform about the circumference of lower ring 1.

In the preferred embodiment of the invention lower ring 1 is also provided with platform 17. In a simple embodiment platform 17 may be integrally formed with, or non-removably attached to ring 1. In preferred embodiment the upper surface of platform 17 will be inclined towards aperture 11 and have an upper surface, where contiguous with ring 1, which is at least as high, and is preferably higher, than upper surface 13 of ring 1; so that fluids on the surface of 13 do not flow onto the surface of platform 17 or tissues stored on platform 17. In preferred embodiment the width and length of platform 17 will be sized to form an upper surface at least as large as the tissues to be temporarily removed from stromal bed 31 (which in the case of LASIK will typically remain attached to the cornea as a flap). In preferred embodiment the surfaces of platform 17 will be smooth and its edges rounded, so as to avoid tearing, sticking or cutting of corneal tissue reposed on the platform.

In the aforesaid embodiment platform 17 provides a clean, dry place to repose temporarily removed corneal tissue removed from stromal bed 31, rather than laying said tissue on the sclera, where it becomes exposed to cud-de-san fluids, as is now commonly done, particularly in LASIK. It is becoming increasingly recognized that when said tissue is laid on the sclera it may encounter a plurality of undesirable conditions, including but not necessarily particulate debris, chemical residue, bacteria and over-hydration of the flap may occur (which may cause the flap to swell and not fit back in place without wrinkles). Any or all of these conditions can lead to "DLK"(diffuse lamellar keratitis) or micro and macro strial of the cornea.

In addition to providing a clean and dry place to repose temporarily removed tissues, platform 17 can aid the surgeon replace the tissues with less "handling" than trying to lift the tissues off the sclera to replace them. That is, at the conclusion of application of the laser, and cleansing of the tissue, lifting the lower ring from the eye, in a sweeping direction over stromal bed 31 will tend to slide the corneal flap off of platform 17 and onto the stromal bed 31.

However, platform 17 may have other attributes to better facilitate the tasks the physician must accomplish. For instance, platform 17 may be releasably attached to lower ring 1. If so attached, then by releasing platform 17 the surgeon may sweep it alone over stromal bed 31 to replace flap 32 on said bed, while maintaining lower ring 1 in place (thus maintaining isolation of the area inside aperture 11 from cul-de-sac fluids until the removed tissues are replaced over stromal bed 31). Various means may be employed to make platform 17 releasably attached, such as notching the lower surface of platform 17 to mate with a section of ring 1, the converse (that is notching a section of ring 1 to mate with the platform), protuberances (such as pins) on the upper surface 13 of lower ring 1 which mate with holes in the lower surface of platform 17, protuberances (such as pins) on the lower surface of platform 17, which fit holes (including possibly ports 14) in the; upper surface 13 of lower ring 1 or other well known means for releasably attaching two rigid members.

In another embodiment, platform 17 may be movably disposed from lower ring 1 along a pre-determined path which is designed to facilitate replacement of removed tissues, such as flap 32, to stromal bed 31. In preferred embodiment this is accomplished by slidably attaching-platform 17 to guide rails 171 as shown in FIG. 4c. In another embodiment platform 17 may be attached by pivot arms 172 as is shown in FIG. 4d. Whatever means may be used to guide the movement of platform 17, it is preferred that the platform increasingly tilt toward the stromal bed 31 as the platform moves across said stromal bed, but not so much that the tissue slides off prematurely, as some dragging the tissue from platform 17 is desired so as to smoothly stretch the removed tissue, such as flap 32, over stromal bed 31 without wrinkles in the tissue.

Whether platform 17 be non-releasably attached, releasably attached, or movable from lower ring 1 along a pre-determined path, platform 17 may have other characteristics to facilitate the surgeon's tasks. The upper surface of platform 17 may contain a plurality of lands and grooves to facilitate introduction of liquid between the platform and tissue disposed on said upper surface, to facilitate "floating" the flap free of the platform. Platform 17 may also have a passageway 174 extending from one of its edges, preferably the radially outward edge, to the upper surface of the platform 17, to facilitate introduction of fluid between said upper surface of the platform and tissue disposed on said upper surface.

Figure 5:
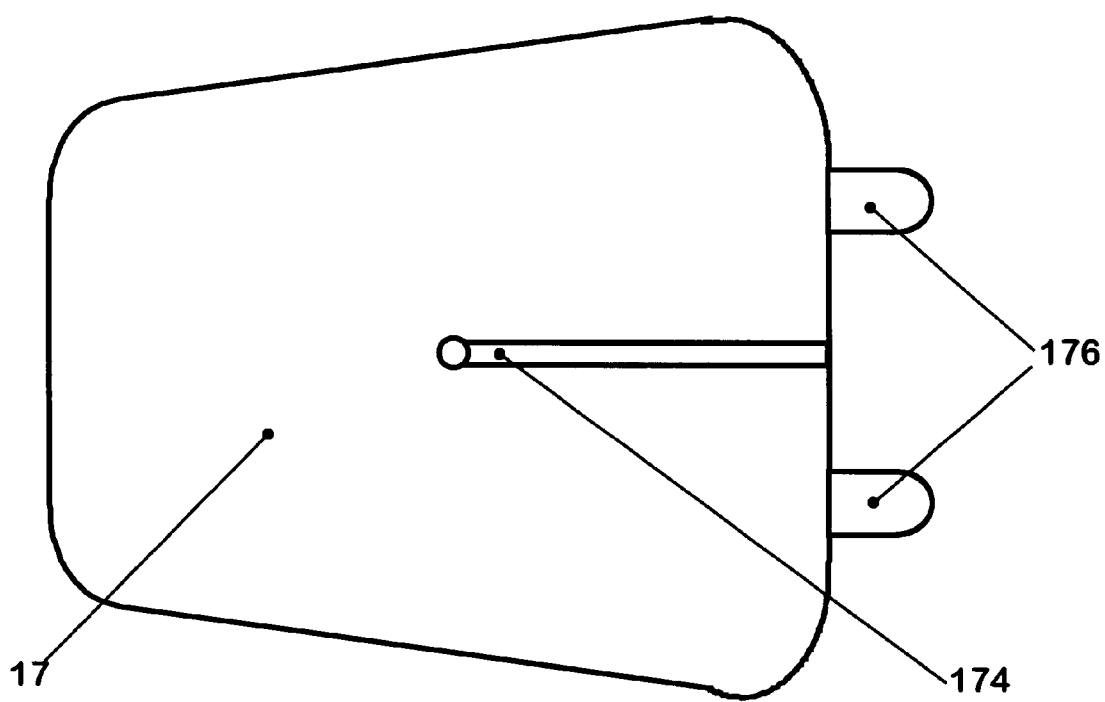
FIG. 5 is an overhead plan view of one embodiment of the platform of the lower ring of the invention disclosed and claimed herein .

When releasably attached platform 17 may be provided with means to engage it with a handtool, so as to facilitate gripping and handling of said platform, such as tab 175 (FIG. 3b), pin 176 (FIG. 5), or hole 177 (FIG. 3b). Preferred is hole 177 where a right angled pick (or similar tool) may be inserted to remove and manipulate platform 17 as desired. Or, if passageway 174 (FIG. 5) is included on platform 17, that can be used in lieu of 177 for attachment of a hand tool, so as to remove and manipulate platform 17.

The primary function of upper ring 2 is to remove smoke, plume and splatter from the surgical field, but it also enhances air flow over the surgical field to help control excess hydration. In the preferred embodiment upper ring 2 may be a generally circular length of rigid tubing, connected to vacuum means attached to tube 21. Ports 22 extend through the wall of said ring. While other dispositions of ports 22 is comprehended by the invention (such as ports disposed about the outer circumference, at the bottom or top of the tubing) in the preferred embodiment of the invention ports 22 are disposed facing radially inward, on the inner circumference of said tubing. As above, said ports may increase in size in proportion to increased distance from tube 21 in order to produce a more uniform airflow around the ring. Increasing intensity of the vacuum applied to the tube 21 increases air flow and enhances removal of smoke, plume and splatter.

While upper ring 2 may constitute a full circle (and this embodiment is comprehended by the invention), in the preferred embodiment upper ring 2 does not constitute a full circle, but is only a segment thereof having closed ends, which does not extend above platform 17 (so as to facilitate access to platform 17 by the surgeon).

In most cases upper ring 2 will be disposed approximately 3–30 millimeters above upper surface 13 of lower ring 1. There it may be attached to tube 16 or to a handle or separate frame (not shown) which is also attached to lower ring 1. Upper ring 2 may be attached to a fixed position on any of said structures, or it may be slidably disposed thereon in the direction to and from lower ring 1 (so that the distance between lower ring 1 and upper ring 2 may be varied as circumstances may require). Upper ring 2 may also be made removably attached to any of said structures, so that the surgeon can remove it when desired.

Figure 4A:
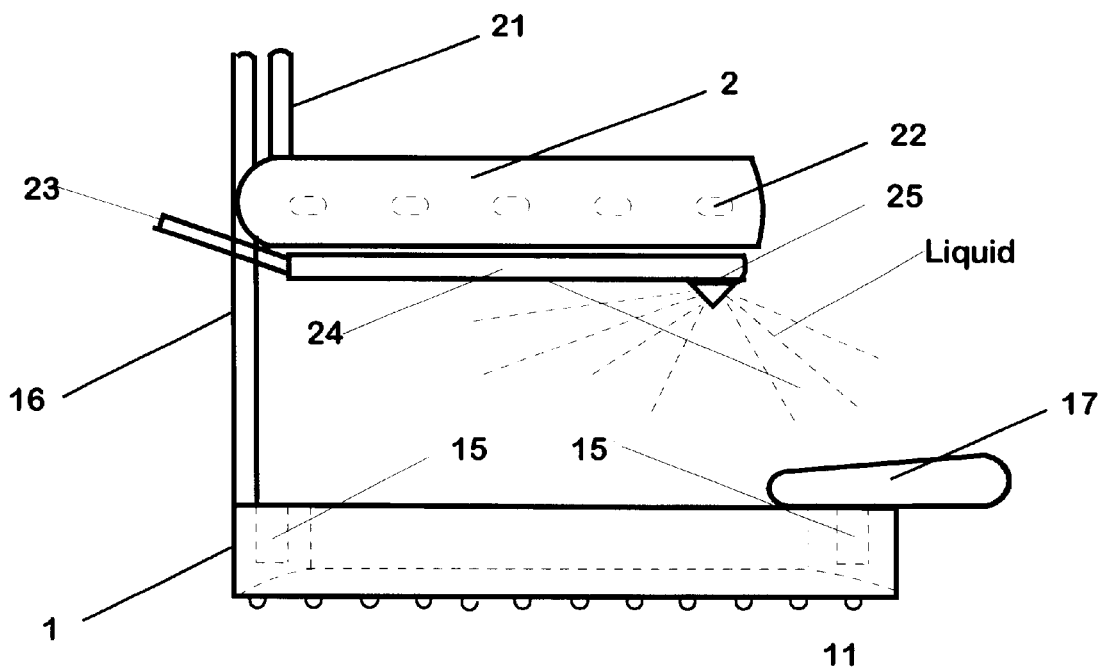
FIG. 4a is an elevational view of an alternative embodiment of the present invention.

Shown in FIG. 4a, is an alternative embodiment of the invention disclosed and claimed. This embodiment may be equipped with means to dispense a liquid onto the surgical bed. While it may be used at other times, this feature of the invention has particular utility to wash debris from the stromal bed and the exposed underside of the corneal flap following completion of ablative procedures, but before return of the corneal flap to the stromal bed. In the preferred embodiment of this alternative liquid is fed through port 23 to semi-circular tube 24 disposed below lower ring 2. Alternatively semicircular tube 24 may be disposed above, outside of, inside of or within lower ring 2. From semi-circular tube 24 liquid may be sprayed from nozzle 25 when desired. Preferably nozzle 25 is above the edges of platform 17, as is shown in FIG. 4a, to facilitate the spraying of liquid onto the underside of corneal flap 32, as it lays exposed on platform 17, and facilitate spray of liquid onto the exposed stromal bed 31 as well. However other positioning of nozzles 25 are comprehended by the invention, its essence being to be able to dispense irrigation liquids downward, from lower ring 2, onto open tissues of the cornea, prior to closure of said tissues.

Figure 4B:
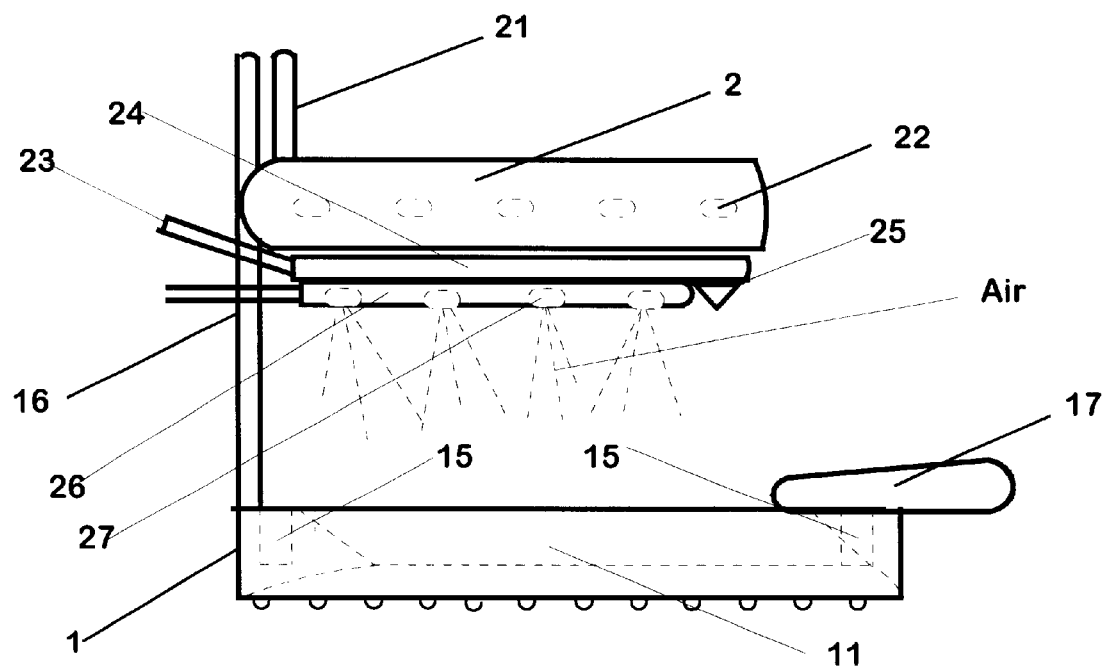
FIG. 4b is an elevational view of another alternative embodiment of the present invention.
Figure 4C:
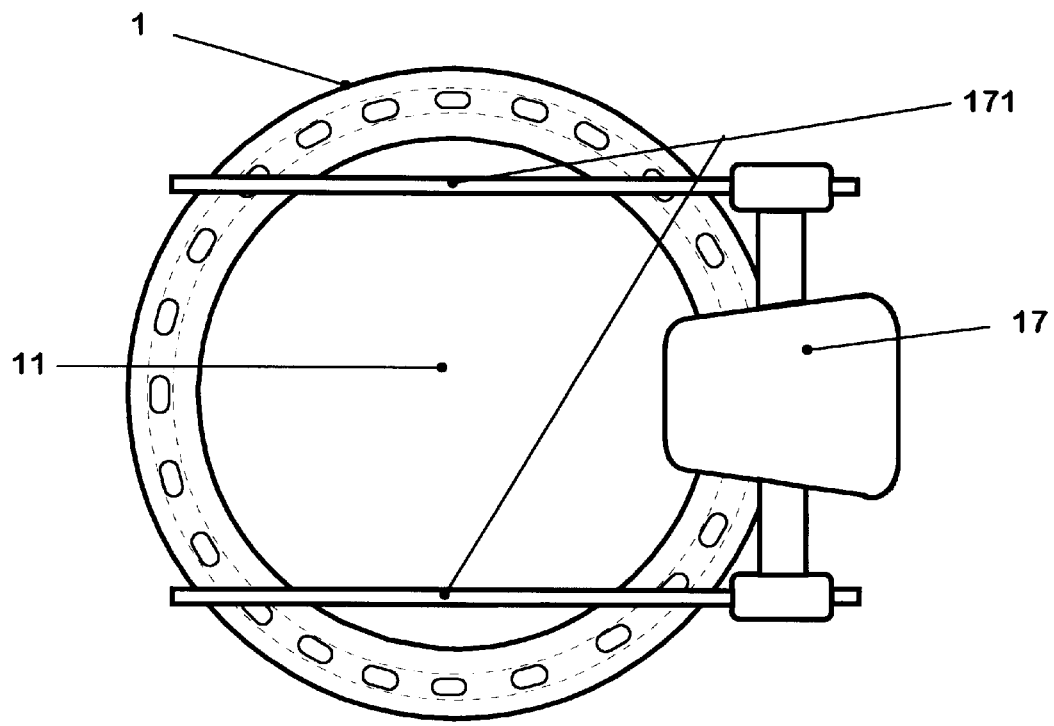
FIG. 4c is an elevational view of another alternative embodiment of the present invention.
Figure 4D:
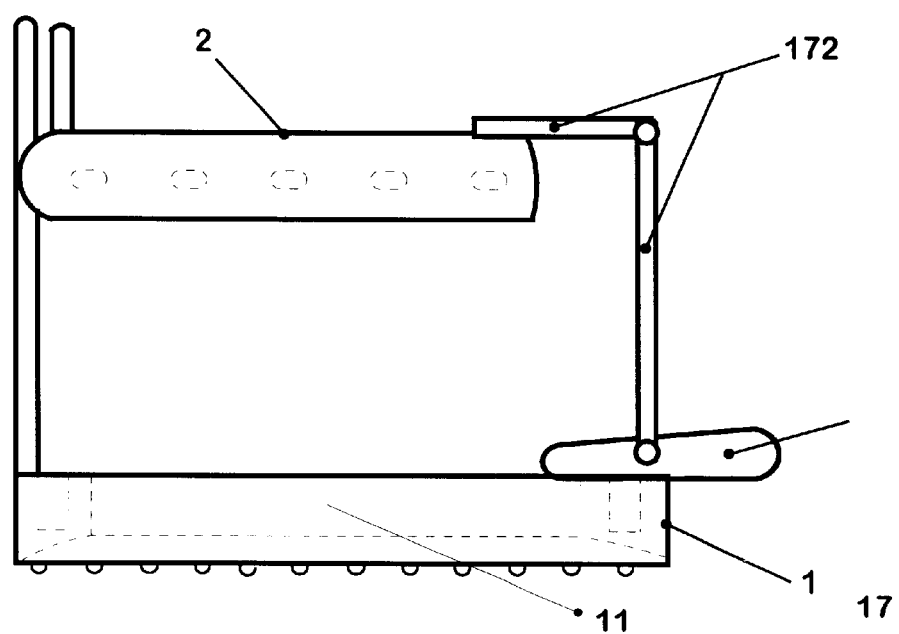
FIG. 4d is an elevational view of another alternative embodiment of the present invention.

In yet another embodiment of the invention, shown in FIG. 4b, lower ring 2 may also be equipped with means to blow a gas, such as oxygen, air or such other gas as may be desired, onto the open stromal bed 31 of the eye, as may be desired or required. As suggested earlier, during ablation of the stromal bed 31, excessive and uneven hydration of the stromal bed can and does occur, and cause subsequent application of laser energy to be unevenly applied. This is, of course, undesirable. Accordingly an alternative embodiment of the invention may include means to blow a, preferably dry and sterile, gas onto the stromal bed 31 to reduce hydration of the tissues of said bed. Blowing of said gas will also aid in removal of smoke, plume and splatter, and gas such as oxygen may have a beneficial effect on said tissues. In this alternative the gas is directed downwardly and toward the center of aperture 11. As shown in FIG. 4b this may be accomplished by a semi-circular tube 26 having closed ends which is disposed below ring 2 and has a plurality of ports 27 which are directed towards the stromal bed 31. In other embodiments gas may be routed to ports 27 by passageway contained above, outside of, inside of or within lower ring 2, the essence of this embodiment of the invention being to provide a means, for use in combination with the other attributes of the invention, to blow a gas onto stromal bed 31 when the ophthalmic surgeon believes that doing so will be efficacious during corneal surgery of the eye.

The preferred embodiment of the invention is preferably used with platform 17 disposed nasally, as it is easiest to form the corneal flap 32 with a nasal hinge. But it may be rotatably disposed about the limbus as the particular surgeon may prefer. It will be typically applied to the eye after creation of a corneal flap (typically by microkeratome). After application of the instrument to the eye, the corneal flap will typically be lifted, directly from the stromal bed, onto platform 17, which is sterile. Disposed on platform 17 the corneal flap may be draped with a wet, surgical sponge or other sterile covering to protect it from tissue debris resulting from ablation to follow. Following this, the surgeon will typically apply a desired amount of vacuum to lower ring 1 and upper ring 2, and then use the instrument to fix the position of the eye as required during application of laser pulses. In the simplest form fixing the position of the eye may be by means of the surgeon holding the instrument of the present invention in place with another instrument or by handle attached to the instrument of the present invention, but other forms of positioning mechanisms, including magnetic means, may also be utilized. During the ablative procedure the surgeon may adjust the intensity of vacuum on one or both rings, as he may find effective to control hydration of the stromal bed and remove smoke, plume and splatter caused by ablation. At the conclusion of the ablative procedure the stromal bed and other tissues of the eye will typically be thoroughly rinsed to remove ablated tissue and other debris thereon. Typically vacuum will be left on lower ring 1 during rinsing to help remove debris containing liquids from the stromal bed and help prevent debris containing liquid from outside of the surgical field from entering the stromal bed. Following thorough rinsing of the eye (including the corneal flap), the corneal flap will be "floated" so as to make sure it is not stuck to the platform then replaced over stromal bed by lifting lower ring from the eye and sweeping the instrument over the stromal bed, or leaving the lower ring in place and moving only the platform over the stromal bed.

It is thus to be appreciated that apparatus in accordance with the principles and teachings of the present inventive disclosure constitutes an advancement in the field of art to which the invention pertains. While the above description contains certain specificities, these should not be construed as limitations on the scope of the invention, but rather as an exemplification of preferred embodiments thereof. Accordingly, the scope of the present invention should be determined not by the embodiments illustrated, but by the appended claims and their legal equivalents.

What is claimed is:

1. A surgical instrument, for placement around the limbus of the eye during corneal surgery by laser, comprising:
   a. a lower ring having a vertical axis, an upper surface, a lower surface curved to substantially match the curvature of the eye outside of the limbus, a thickness between said upper surface and said lower surface, an outer diameter; and, a central aperture substantially sized to fit about the limbus of the eye; all together defining a disc shaped structure having a central aperture surrounded by an annular wall;
   b. wherein said lower ring includes a platform having an upper surface which has an area at least the size of a hinged corneal flap to be created in the course of said corneal surgery, which said upper surface of said platform extends radially outward from an inner diameter of said lower ring which is proximate to the hinge of said corneal flap and is disposed at a height which is above the lower surface of said lower ring where said lower surface of said lower ring intersects with the outer diameter of said lower ring; and,
   c. means for movably attaching said platform to a segment of said lower ring.

2. The surgical instrument of claim 1 wherein said means for attaching of said platform to said lower ring is releasable.

3. The surgical instrument of claim 2 wherein said means for attaching said platform to said lower ring is comprised of a notch on the lower surface of said platform which mates with said segment of said lower ring.

4. The surgical instrument of claim 2 wherein said means for attaching said platform to said lower ring is comprised of a notch on the upper surface of said lower ring which mates with at least a portion of the lower surface of said platform.

5. The surgical instrument of claim 2 wherein said means for attaching said platform to said lower ring is comprised of a protrusion on the lower surface of said platform which mates with a hole in the upper surface of said lower ring.

6. The surgical instrument of claim 2 wherein said means for attaching said platform to said lower ring is comprised of a hole on the lower surface of said platform which mates with a protrusion in the upper surface of said lower ring.

7. The surgical instrument of claim 2, wherein said platform further comprises means for engagement of a hand tool with said platform.

8. The surgical instrument of claim 7 wherein said means for engagement of a hand tool is comprised of a protrusion adapted to engage with a hand tool.

9. The surgical instrument of claim 7 wherein said means for engagement of a hand tool is comprised of a hole adapted to engage with a hand tool.

10. The surgical instrument of claim 2, further comprising a means for guiding said platform along a predetermined course of movement.

11. The surgical instrument of claim 10, wherein said means for guiding said platform is comprised of at least one guide rail to which said platform is movably engaged.

12. The surgical instrument of claim 10, wherein said means for guiding said platform is comprised of at least one arm to which said platform is pivotally engaged.

13. A surgical instrument, for placement around the limbus of the eye during corneal surgery by laser, comprising:
    a. a lower ring having a vertical axis, an upper surface, a lower surface curved to substantially match the curvature of the eye outside of the limbus, a thickness between said upper surface and said lower surface, an outer diameter; and, a central aperture substantially sized to fit about the limbus of the eye; all together defining a disc shaped structure having a central aperture surrounded by an annular wall;
    b. wherein said lower ring includes a platform having an upper surface which has an area at least the size of a hinged corneal flap to be created in the course of said corneal surgery, which said upper surface of said platform extends radially outward from an inner diameter of said lower ring which is proximate to the hinge of said corneal flap and is disposed at a height which is above the lower surface of said lower ring where said lower surface of said lower ring intersects with the outer diameter of said lower ring; and,
    c. means for releasably attaching said platform to a segment of said lower ring.

14. The surgical instrument of claim 13 wherein said platform further comprises a liquid transmissible passageway extending from said upper surface to an edge of said platform.

15. The surgical instrument of claim 13 wherein said means for attaching said platform to said lower ring is comprised of a notch on the lower surface of said platform which mates with said segment of said lower ring.

16. The surgical instrument of claim 13 wherein said means for attaching said platform to said lower ring is comprised of a notch on the upper surface of said lower ring which mates with at least a portion of the lower surface of said platform.

17. The surgical instrument of claim 13 wherein said means for attaching said platform to said lower ring is comprised of a protrusion on the lower surface of said platform which mates with a hole in the upper surface of said lower ring.

18. The surgical instrument of claim 13 wherein said means for attaching said platform to said lower ring is comprised of a hole on the lower surface of said platform which mates with a protrusion on the upper surface of said lower ring.

19. The surgical instrument of claim 13, wherein said platform further comprises means for engagement of a hand tool with said platform.

20. The surgical instrument of claim 19 wherein said means for engagement of a hand tool is comprised of a protrusion adapted to engage with a hand tool.

21. The surgical instrument of claim 19 wherein said means for engagement of a hand tool is comprised of a hole adapted to engage with a hand tool.

22. The surgical instrument of claim 13, further comprising a means for guiding said platform along a predetermined course of movement.

23. The surgical instrument of claim 22, wherein said means for guiding said platform is comprised of at least one guide rail to which said platform is movably engaged.

24. The surgical instrument of claim 22, wherein said means for guiding said platform is comprised of at least one arm to which said platform is pivotally engaged.

* * * * *